United States Patent
Nelson et al.

[11] Patent Number: 5,158,088
[45] Date of Patent: Oct. 27, 1992

[54] ULTRASONIC DIAGNOSTIC SYSTEMS FOR IMAGING MEDICAL INSTRUMENTS WITHIN THE BODY

[75] Inventors: Kip R. Nelson, Bothell, Wash.; Howard Fidel, Hartsdale, N.Y.; Joseph D. Aindow, Dorchester, England

[73] Assignee: Advanced Technology Laboratories, Inc., Bothell, Wash.

[21] Appl. No.: 613,186

[22] Filed: Nov. 14, 1990

[51] Int. Cl.⁵ .............................................. A61B 8/12
[52] U.S. Cl. ........................... 128/662.05; 128/662.06
[58] Field of Search ...................... 128/660.01, 662.05, 128/662.06

[56] References Cited
U.S. PATENT DOCUMENTS

| | | | |
|---|---|---|---|
| 3,556,079 | 1/1971 | Omizo | 128/662.05 |
| 4,249,539 | 2/1979 | Vilkomerson et al. | 128/662.05 |
| 4,346,717 | 8/1982 | Haerten | 128/662.05 |
| 4,407,294 | 1/1982 | Vilkomerson | 128/662.05 |
| 4,501,277 | 2/1985 | Hongo | 128/660.05 |
| 4,567,896 | 2/1986 | Barnea et al. | 128/662.05 |
| 4,671,292 | 6/1987 | Matzuk | 128/662.05 |
| 4,694,680 | 9/1987 | Takeuchi et al. | 128/660.01 |

FOREIGN PATENT DOCUMENTS

2157828 3/1987 United Kingdom .

*Primary Examiner*—Francis Jaworski
*Attorney, Agent, or Firm*—W. Brinton Yorks, Jr.

[57] ABSTRACT

An ultrasonic imaging system for guiding a user in the placement of a medical instrument within the body is described. As the medical instrument approaches the image plane of an imaging transducer, ultrasonic wave energy is received by a transducer located on the medical instrument. The level of received energy is detected and used to develop a control signal which varies as a function of the quantum of received energy. The control signal is used to modulate an audible indicator, which provides an audible indiction of proximity of the medical instrument to the image plane as the instrument approaches and intersects the plane. A visual marker is produced on an image display which represent the location of the instrument within the body. As the instrument approaches and intersects the image plane the visual marker is also modulated. The system includes a test and calibration mode of operation, which exercises components of the medical instrument transducer signal processor, and also transmits calibration signals to the image display for calibration and verification purposes prior to the commencement of a medical procedure.

20 Claims, 6 Drawing Sheets

ULTRASONIC DIAGNOSTIC SYSTEMS FOR IMAGING MEDICAL INSTRUMENTS WITHIN THE BODY

This invention relates to ultrasonic diagnostic systems which noninvasively image internal parts of the body and, in particular, to the use of such systems for guiding the placement of a medical instrument within the body.

Ultrasonic diagnostic imaging systems may be used in conjunction with surgical and other invasive procedures to assist in the locational placement of medical instruments inside the body. For example, U.S. Pat. Nos. 4,697,595 and 4,706,681 describe cardiac catheters and pacing leads carrying ultrasonic transducers. When these devices are used in conjunction with an ultrasonic imaging system, the location of the catheter or leads inside the body can be represented in the ultrasonic image by the reception or transmission of ultrasonic signals between the imaging transducer and the transducer mounted on the invasive device.

This technique of incorporating ultrasonic transducers into invasive medical instruments has also been applied to needle-type devices, as illustrated in U.S. Pat. No. 3,556,079 (Omizo) and U.S. Pat. No. 4,249,539 (Vilkomerson et al.) In the Omizo patent, Doppler interrogating waves are directed forward from the tip of a needle. As the needle penetrates the body, backscatter waves from moving fluids within a vessel or organ are received and a conventional Doppler beat frequency is detected. The reception of the Doppler tone provides an indication that the needle is aimed at the vessel or organ containing the fluid; if the needle becomes misdirected, no backscatter waves are returned and the Doppler tone ceases.

Recognizing the inherent limitations of the highly directional Omizo technique, Vilkomerson et al. provides a system with an omnidirectional transducer located at the needle tip. When used in conjunction with an imaging transducer, the omnidirectional transducer is able to exchange ultrasonic waves with the imaging transducer irrespective of its orientation with the imaging transducer, thereby enabling the Vilkomerson et al. system to continually provide a visual marker in the ultrasonic image which indicates the needle tip location. However, the Vilkomerson et al. system places several critical demands on its user, such as a physician performing a biopsy procedure. An ultrasonic imaging transducer scans over a relatively planar portion of the body, which is depicted in a two-dimensional image. The needle, however, is free to move in three dimensions as it penetrates the body. Hence, the Vilkomerson et al. system operates well for its intended purpose when the needle tip is located within the scan plane, but its operation can be ambiguous when the physician first penetrates the body and attempts to achieve that orientation. Under these initial conditions of the procedure the physician must focus his attention on the insertion and guidance of the biopsy needle as it penetrates the patient's body. At the same time the physician must manipulate the imaging transducer and watch the imaging monitor to simultaneously orient the transducer and needle so that both the tissue structure which is to be biopsied and the needle tip are in the image plane. The simultaneity of both the biopsy procedure and the imaging procedure impose severe demands on even highly skilled practitioners. It would be desirable to provide system features that would ease these demands on the physician during placement of the biopsy needle.

An effort directed toward easing these demands is depicted in U.S. Pat. No. 4,407,294 (Vilkomerson). In the system there shown, a biopsy needle has two detector-transducers located at the needle tip. Ultrasound waves directed toward the needle tip during the biopsy procedure will be received at slightly different times by the two transducers, depending upon the orientation of the needle relative to the imaging transducer. Vilkomerson then performs a phase comparison of the signals received by the two transducers and uses the result of the phase comparison (e.g., lagging or leading phase) to activate either a "move-left" or "move-right" indicator. It is intended that the indicator will provide guidance to the physician as to the manipulation required of either the needle or imaging transducer in order to bring the needle tip into the image plane. However, the patent acknowledges that ambiguity is present in such a system, for "left" or "right" have no absolute meaning. This is because rotation of the needle or the imaging transducer will cause a reversal of the left-right orientation. To overcome this problem, Vilkomerson proposes to provide indicia on the outer end of the needle. The result is, in addition to the aforementioned demands, the physician must further monitor the directional indicators and the needle indicia. Hence, the biopsy procedure can become even more demanding.

In accordance with the principles of the present invention, a system for monitoring the placement of a medical instrument within the body through ultrasonic imaging is provided to simplify instrument placement. An ultrasonic transducer is located at the distal end of the instrument to receive ultrasonic waves from an imaging transducer. When ultrasonic waves are received by the instrument transducer, an audible indicator is sounded. As the instrument transducer approaches the directed paths of the ultrasonic waves, the intensity of the received ultrasonic energy increases, and the audible sound is modulated accordingly. Hence, the physician can monitor the progress of the insertion procedure audibly, while visually monitoring instrument insertion and the target location within the body.

The received ultrasonic waves are further used to provide a visual marker on an ultrasonic image display to indicate the position of the instrument transducer within the body. In accordance with a further aspect of the present invention, the visual marker is modulated as a function of received ultrasonic energy, providing visual guidance of the proximity of the instrument to the image plane.

In accordance with yet a further aspect of the present invention, the system includes a test and calibration mode of operation. This mode of operation provides a test of subsystems of the system which processes signals received by the instrument transducer. The mode of operation further provides calibration markers on the image display, allowing calibration of the ultrasonic image display to insertion depths of the medical instrument prior to commencement of any invasive procedure.

Figure 1:
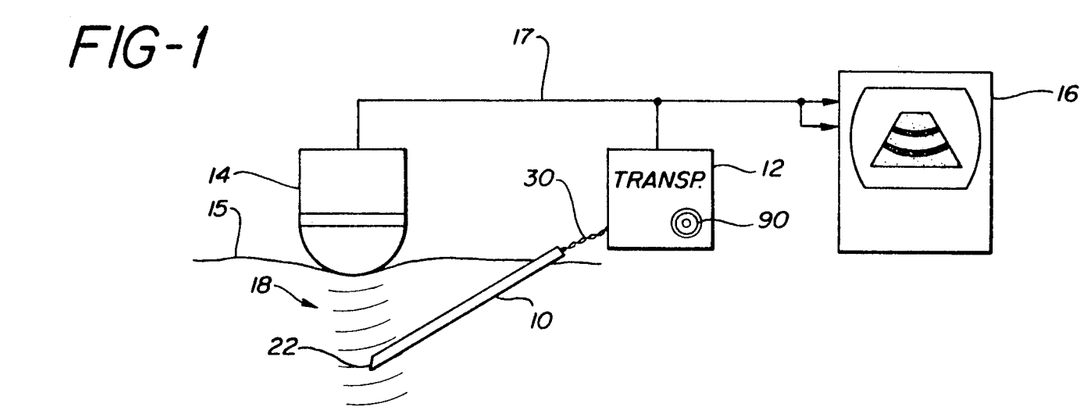
FIG. 1 illustrates a system for ultrasonically imaging a biopsy needle which is constructed in accordance with the principles of the present invention.

Referring first to FIG. 1, a system constructed in accordance with the principles of the present invention for ultrasonically imaging placement of a biopsy needle is shown. A hollow biopsy needle 10 is shown emplaced in the body of a patient, having penetrated skin surface 15. The hollow needle carries within it an invasive biopsy probe configured as a stylet 20 (shown in FIG. 2) which has an ultrasonic transducer 22 made of PVDF material affixed to the distal tip of the stylet. Ultrasonic waves 18 emanate from the transducer of an ultrasonic imaging probe 14 and are directed toward the region of the body being biopsied. The probe's transducer is energized by transmit pulses provided by the imaging system 16 by way of cable 17, and ultrasonic echo information received by the imaging probe transducer are transmitted back to the imaging system by way of the cable where they are used to form a planar image of the body region. The ultrasonic waves produced by the imaging probe may be steered electronically through use of a multielement transducer, or the waves may be steered mechanically by a mechanism in the probe which rotates or oscillates the transducer. The appropriate signals needed to steer the ultrasonic waves are also conveyed by way of the cable 17.

As ultrasonic waves are received by the stylet transducer 22 they are converted to electrical signals by the transducer, which signals are conveyed by wiring within the stylet and external thereto as shown at 30 to a transponder module 12. In response to these received signals the transponder module will produce an audible sound by means of a speaker 90, and will generate a video marker signal indicating the position of the transducer 22 in the image plane of the imaging probe 14. The video marker signal is transmitted by connection to cable 17 to the image display of the ultrasonic imaging system 16 where it it displayed at the proper location on the display. As will be explained in detail below, both the audible sound of the speaker 90 and the displayed video marker are modulated in accordance with the intensity of the ultrasonic energy received by the transducer 22. This provides the user with both audible and visual indications of the proximity of the needle tip to the planar region of the body which is being imaged.

Figure 2:
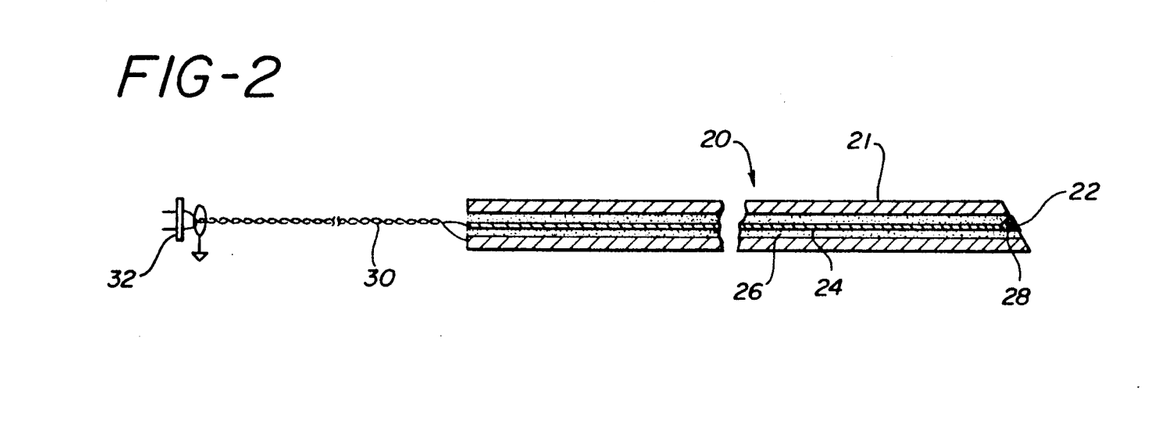
FIG. 2 illustrates a biopsy needle stylet with an ultrasonic transducer at the tip of the stylet.

The stylet 20 is shown in partial cross-sectional view in FIG. 2. The stylet includes a hollow body 21 of stainless steel. Carried within the hollow central area of the body is a copper wire 24 which is surrounded by an epoxy resin 26 to insulate the wire from the stainless steel body. At the distal tip of the stylet 20 is a transducer 22 made of PVDF film. The back surface of the transducer is attached to the copper wire by a UV cured epoxy 28, providing a capacitive electrical coupling between the back surface of the transducer 22 and the wire. No physical connection is made to the front surface of the transducer, which is galvanically coupled to the stainless steel body. As ultrasonic waves are received by the transducer, they are converted to differential signals carried by the wire 24 and the body 21 to shielded twisted pair wires 30 at the proximal end of the stylet. At the end of the twisted pair wires is a connector 32 which connects to the transponder module 12. In a constructed embodiment of the stylet of FIG. 2, the transducer 22 comprised a piece of PVDF film having a diameter of seven thousandths of an inch and a thickness of 52 micrometers. This substantially planar profile of the transducer against the tip of the stylet and backed by epoxy causes the transducer to exhibit a substantially conical antenna profile oriented in the forward direction from the stylet tip.

Figure 3:
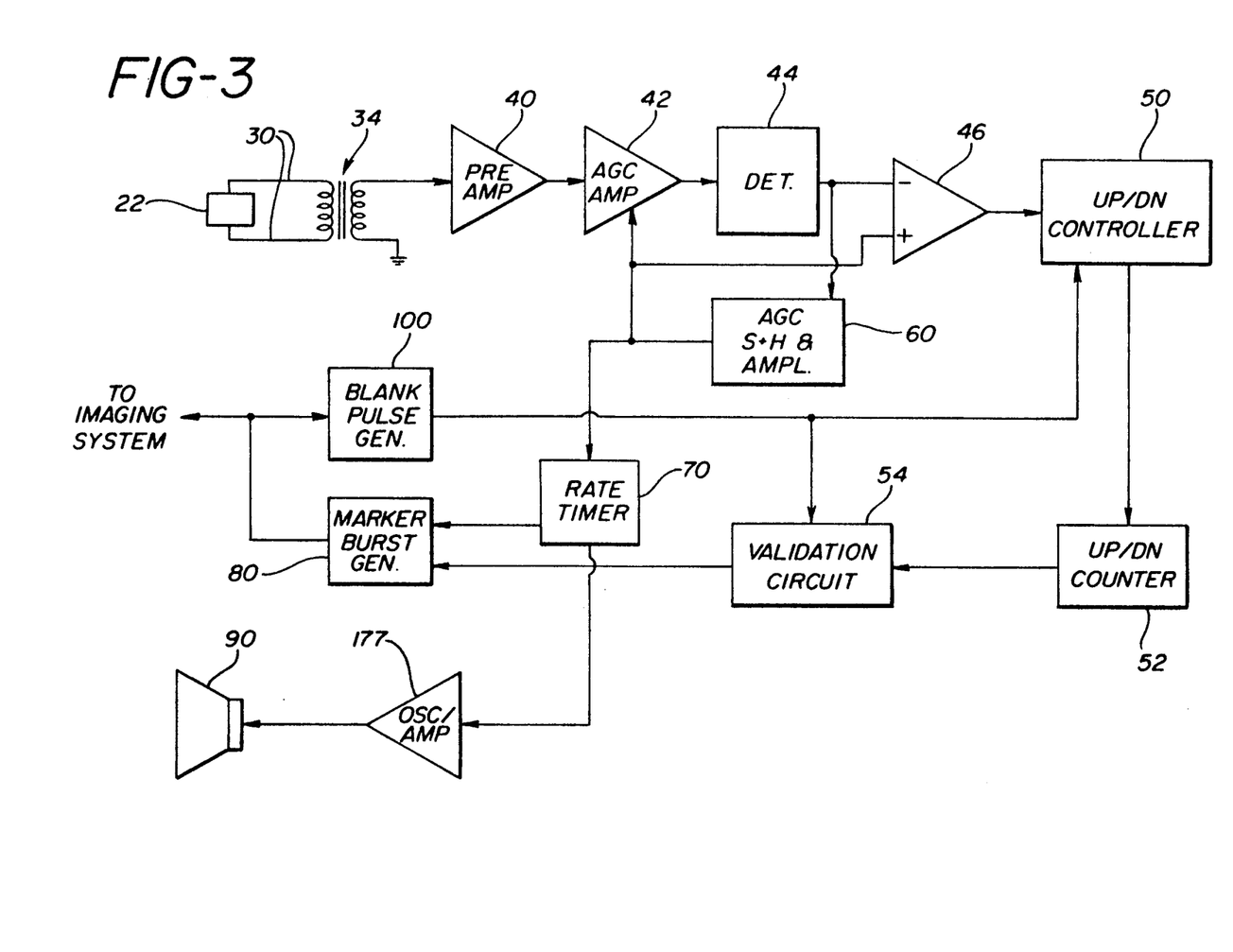
FIG. 3 illustrates in block diagram form a system for receiving and processing ultrasonic energy from a medical instrument transducer in accordance with the principles of the present invention.

FIG. 3 illustrates in block diagram form the processing circuitry of the transponder module 12. The transducer 22 of the stylet is connected by the wires 30 to the primary winding of a transformer 34. The transformer 34 provides direct current electrical isolation between the stylet and the module circuitry. Signals developed by the transducer 22 in response to ultrasonic wave energy received from the imaging probe are thus transformer coupled to the input of a preamplifier 40. The output of the preamplifier is coupled to the input of an automatic gain control (AGC) amplifier 42. Ultrasonic energy signals amplified by the gain characteristic of the AGC amplifier are detected by a full wave amplitude detector 44. The detected signals are applied to an AGC sample and hold amplifier circuit 60 which samples the detected signals and develops an AGC control voltage in proportion to the level of the detected signals. The detected signals are also applied to one input of a comparator 46, where the signal level is compared with the AGC control voltage level. The comparator 46 produces a pulse in response to detected signals which exceed the variable threshold of the AGC voltage. These detected pulses are then applied to an up/down controller 50 for further processing. The AGC control voltage is also applied to the gain control input of the AGC amplifier 42 and to a rate timer 70. The rate timer 70 produces modulating signals proportional to the AGC control voltage for a marker burst generator 80 and an oscillator/amplifier 177. The oscillator/amplifier produces an audible tone through a speaker 90 which is modulated by the modulating signal from the rate time.

Detected pulses produced by the comparator 46 are processed for display of a video marker signal on the image display. The processing begins with reception of transmit pulses for the imaging transducer which are received at the input of blank pulse generator 100 by way of cable 17. Each transmit pulse causes the blank pulse generator 100 to produce a pulse which causes the up/down controller 50 to load initializing data into an up/down counter 52. The counter 52 then begins counting up from the initialized count. Upon receipt of a pulse from the comparator 46, indicating time of reception of an ultrasonic wave by the stylet transducer, the up/down controller causes the direction of the count to reverse and the counter 52 begins to count back toward zero. A count of zero indicates the full transit time for an ultrasonic wave to reached the stylet tip, and for an echo to return from the stylet tip to the imaging transducer. Thus, this full transit time as determined by the counter 52 marks the time at which a marker should be sent to the imaging system to mark the location of the stylet tip in the image.

A validation circuit 54 is synchronized by pulses from the blank pulse generator 100 and in concert with controller 50 and counter 52 acts to validate marker information for display. The output of the validation circuit is coupled to an input of marker burst generator 80 which produces marker burst signal suitable for detection by the imaging system. The marker burst signal is modulated by a signal from the rate timer so that the displayed marker will provide a visual indication of proximity of the stylet tip to the image plane. The marker burst signal is applied to the imaging system by the same cable 17 that delivers the transmit pulses to the blank pulse generator.

Figure 4:
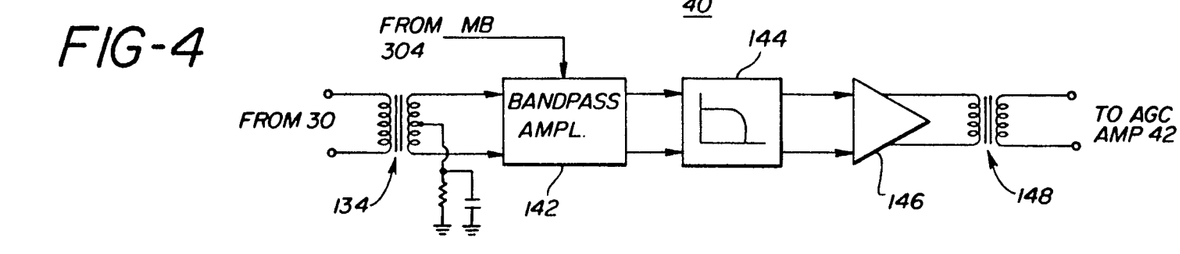
FIG. 4 is a detailed schematic drawing of the preamplifier of the system of FIG. 3.

Referring to FIG. 4, the preamplifier 40 and isolation transformer are shown in greater detail. The differential ultrasonic wave energy signals carried by the twisted pair wires 30 are applied to the primary winding of transformer 134. The secondary of the transformer is coupled to a low Q bandpass amplifier 142, which passes information signals in the passband to a lowpass filter 144. The lowpass filter 144 has a cutoff frequency chosen to remove signals above frequencies of interest in the ultrasonic energy signals for better noise immunity. The filtered signals are amplified by a differential amplifier 146 and coupled by a transformer 148 to the AGC amplifier 42.

Figure 5:
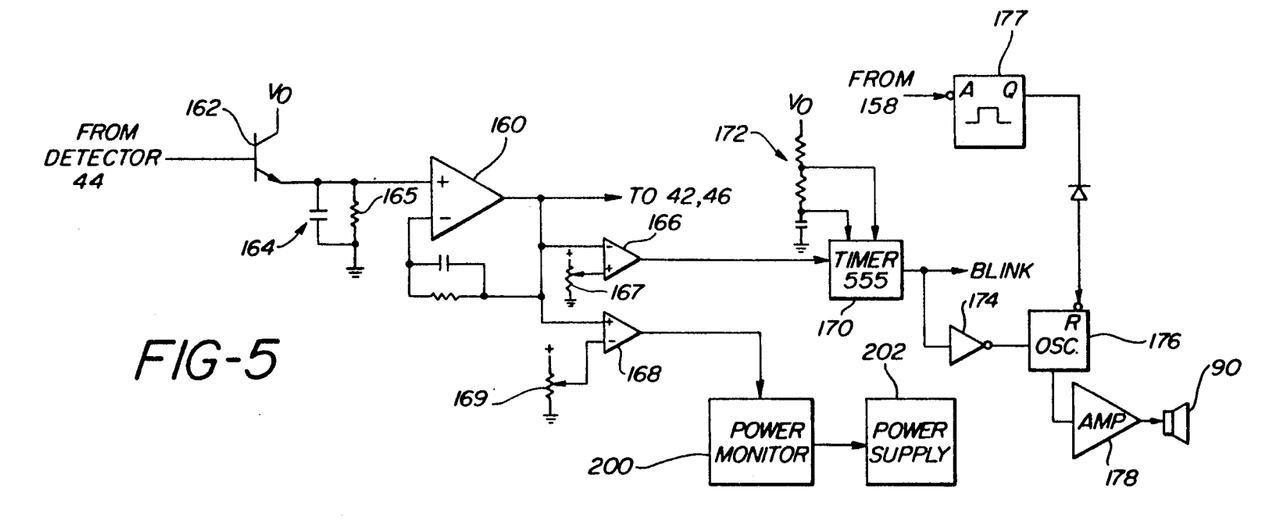
FIG. 5 is a detailed block and schematic drawing of the AGC and indicator modulation subsystems of the system of FIG. 3.

The AGC circuitry and audio and video modulating signal circuitry is shown in schematic form in FIG. 5. Detected ultrasonic wave information signals from the detector 44 are coupled to the base of a transistor 162, causing the level of the signals to be sampled to charge a time constant network including capacitor 164 and resistor 165. The capacitor is rapidly charged by the transistor to substantially the peak of the detected ultrasonic waves and slowly discharged by resistor 165. A time constant of approximately one second for the network causes the network to sample and accumulate charge from a number of successively received waves. Hence, the voltage level to which the capacitor is charged is a measure of the quantum, or intensity, of ultrasonic wave energy received by the stylet transducer 22 over a period of time. This voltage level signal is amplified by AGC amplifier 160 to generate an ACG control voltage which increases when ultrasonic wave energy is being received and decreases in the absence of ultrasonic wave energy. When the AGC control voltage is applied to the gain control input of the AGC amplifier 42, the amplifier will exhibit maximum gain in the absence of received ultrasonic energy and a reduced gain when the transducer 22 is in the image plane and constantly receiving ultrasonic energy.

The AGC control voltage is also applied to an input of the comparator 46, thereby presenting a relatively low threshold in the absence of ultrasonic wave reception, and an increasing threshold as the transducer 22 approaches and becomes coincident with the image plane.

The AGC control voltage is further applied to inputs of an operational amplifier 166 and a comparator 168. The comparator and operational amplifier also receive reference voltage levels from potentiometers 167 and 169. The output of comparator 168 is coupled to a power monitor 200, which includes a timer that is initialized when power to the transponder module is first turned on. If the power monitor timer times out without a change of state by comparator 168, a condition that would exist after a period of time without reception of ultrasonic wave energy, the power monitor turns off the power supply 202. However, reception of ultrasonic wave energy before the timer times out will increase the AGC control voltage, causing the comparator 168 to change state and reset the timer. This shutdown network will cause the transponder module to be automatically turned off when it is not in operation, permitting the module to be powered by batteries with conservation of the battery power.

The output of operational amplifier 166 will follow the AGC control voltage in inverted fashion. The operational amplifier output voltage is applied to a 555 type timer 170, which has a time constant established by resistor-capacitor network 172. The time constant of the network 172 is chosen so that the timer 170 will produce one Hertz pulses at the limit of the AGC control voltage range extant in the absence of ultrasonic wave detection. As the voltage from the operational amplifier decreases as ultrasonic wave energy is received by the biopsy probe, the frequency of the pulses produced by the timer increases correspondingly toward a maximum frequency of approximately three Hertz. The potentiometer 167 provides a means for manually trimming the rate of this BLINK signal producer by the timer 170.

This varying rate BLINK signal is applied by way of an inverter 174 to another 555 type timer 176, which is configured as a gated oscillator. The oscillator 176 produces gated bursts of three kiloHertz signals, which are amplified by an amplifier 178 to drive speaker 90. In the absence of reception of ultrasonic wave energy by transducer 22, the speaker 90 is inactive. This is because the oscillator 176 becomes enabled only in response to a pulse from monostable multivibrator 177 applied to the reset input of the oscillator. As will be explained below, multivibrator 177 is triggered in response to the validated detection of ultrasonic wave energy, and produces a pulse with a width which is at least greater than the lowest image frame rate of the imaging system. Hence, as the biopsy probe stylet begins to receive a constant succession of ultrasonic waves, the multivibrator 177 will be repetitively triggered so that the oscillator 176 is constantly enabled. Thus, as the stylet tip approaches the scan plane and begins to receive ultrasonic wave energy, the speaker begins to sound at the rate of one tone per second. And as the stylet tip closes with and intersects the image plane, thereby receiving ultrasonic waves in rapid and continual succession, the rate of the tone increases toward a maximum rate of three tones per second. Thus the physician manipulating the biopsy needle and stylet is audibly guided to coincidence with the image plane.

Figure 6:
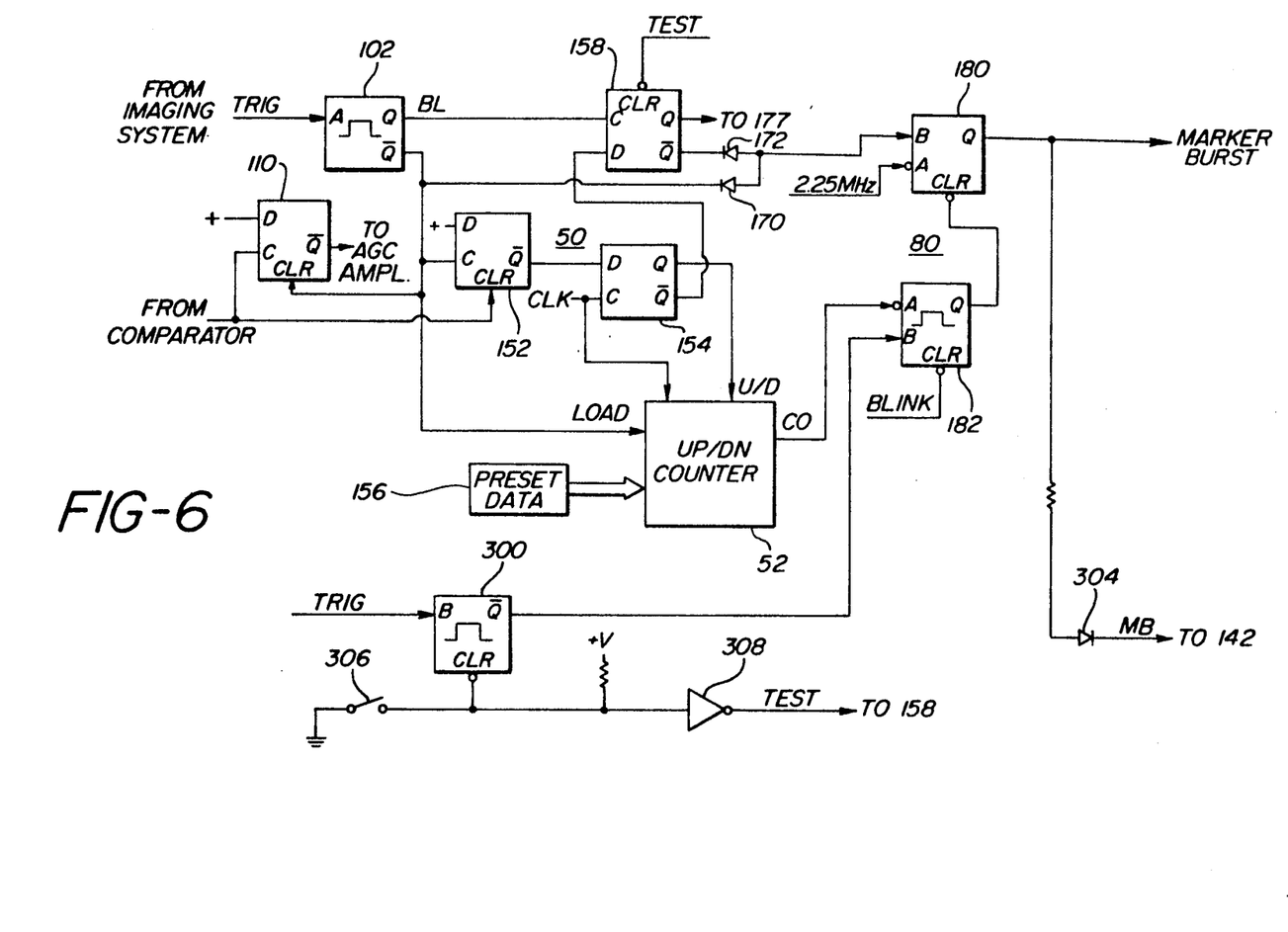
FIG. 6 is a detailed block and schematic diagram of the visual marker and test and calibration subsystems of the system of FIG. 3.

A schematic drawing of the portion of the system which produces a visual marker of the stylet tip location in the ultrasonic image is shown in FIG. 6. As shown in FIG. 1, the transponder module 12 is connected to the cable 17 which carries the transmit pulses from the imaging system 16 to the probe 14, and also the ultrasonic echo returns to the imaging system from the probe. The transmit pulses, labelled TRIG in FIG. 6, are applied to the input of a monostable multivibrator 102. The Q-not output of multivibrator 102 is coupled to the "load" input of up/down counter 52. A pulse at this input loads an initial count into the counter 52 from a preset data register 156. This data value may be selectively adjusted to calibrate the time-of-flight measurement performed by the counter 52.

The Q-not output of multivibrator 102 clears flip-flop 110 and clocks flip-flop 152 to its set state in anticipation of reception of a pulse from the biopsy probe 20. The Q-not output is also coupled by way of a diode 170 to an input of a marker burst monostable multivibrator 180, which prevents any inadvertent triggering of multivibrator 180 in response to receipt of the TRIG pulse from the imaging system or the initialization of counter 52. The setting of flip-flop 152 causes the high frequency system clock CLK to reset flip-flop 154 of the up/down controller and the Q output of this flip-flop will be put in a low state. This output is coupled to the up/down control input of counter 52, which is now controlled to count up. At the end of the duration of the pulse of multivibrator 102 the counter 52 will start to count up from its initial count in response to pulses of the CLK signal. The Q-not output of flip-flop 154, which is now in a high state, is coupled to the D input of validation flip-flop 158, the steady state of which is the set condition. The validation flip-flop 158 is clocked by pulses from the Q output of multivibrator 102, and the Q output of flip-flop 158 triggers the multivibrator 177. If no ultrasonic wave is detected by the biopsy probe 20 in response to the current TRIG pulse, the next TRIG pulse will cause the pulse from multivibrator 102 to set the validation flip-flop 158, and its Q-not output will stay low. This state of the Q-not output of flip-flop 158 will inhibit triggering of the marker burst multivibrator 180.

Upon the receipt of a detectable ultrasonic wave by the biopsy probe 20, the comparator 46 will produce a pulse as previously described. This pulse will set the flip-flop 110. The Q-not output of flip-flop 110 is coupled to the gain control input of the AGC amplifier 42 and the setting of the flip-flop will force the gain of the amplifier to a minimal gain condition. This will prevent reception of noise by the system after an ultrasonic wave is detected or the propagation of marker burst pulses through the AGC amplifier, until the flip-flop 110 is reset in response to the next TRIG pulse.

The pulse produced by the comparator 46 will also clear flip-flop 152 of the up/down controller, forcing its Q-not output to a high state. This state change will be clocked into flip-flop 154 by the next CLK pulse, and the change of state of flip-flop 154 will cause the counter 52 to begin counting down. This change of count direction marks the time of flight of an ultrasonic wave from the imaging probe 14 to the biopsy probe 20. When the counter 52 counts down to a count of zero, a carry-out pulse will be produced at the CO output of the counter, marking the theoretical time of return of an ultrasonic echo from the biopsy probe 20 to the imaging probe 14. It is at this time that a signal should be injected into the echo return path to the imaging system for proper display of a visual marker of the stylet tip in the ultrasonic image. Accordingly, at this time the CO pulse from the counter will trigger monostable multivibrator 182 to produce a pulse which releases the clear input of the marker burst multivibrator 180. However, the multivibrator 180 will not produce a marker burst, as it is inhibited at this time by the low state of the Q-not output of flip-flop 158.

The next TRIG pulse and the resultant pulse produced at the Q output of multivibrator 102 will clock the low state of the Q-not output of flip-flop 154 into the verification flip-flop 158. The Q-not output of flip-flop 158 is now high, and the marker burst multivibrator is no longer inhibited by the verification flip-flop. The multivibrator 177 is also triggered by flip-flop 158, enabling the oscillator 176 to produce the audible tone. Thus, if ultrasonic energy is received by the biopsy probe 20 in response to the current TRIG pulse, the counter 52 will again count up and down, produce a CO pulse, and trigger the multivibrator 182. The pulse produced by multivibrator 182 gates the multivibrator 180 and the 2.25 MHz pulse train at the A input of the multivibrator 180 will cause the multivibrator 180 to produce a sequence of 70 nanosecond pulses for the two microsecond duration of the pulse from multivibrator 182.

Figure 7:
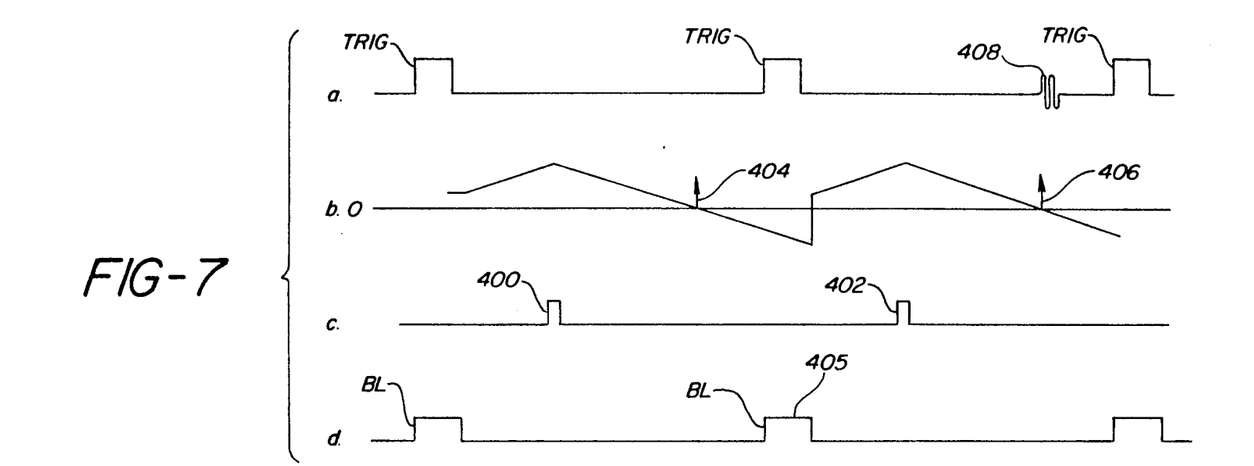
FIGS. 7-9 illustrate waveforms depicting the operation of the system of FIGS. 3-6.

The foregoing sequence of operation is depicted in the waveforms of FIG. 7. The received TRIG pulses are shown in waveform 7a, and the corresponding pulses BL produced by the multivibrator 102 are shown in waveform 7d. Waveform 7b depicts the count of the counter 52, which is seen to be set to an initial value at the end of the BL pulses. The counter then counts up until a pulse 400 is received from comparator 46 (FIG. 7c), at which time the counter begins to count down. Arrow 404 marks the time that a CO pulse is produced, but no marker burst is produced at this time due to the state of the validation flip-flop. The second BL pulse 405 changes the state of the validation flip-flop just prior to clocking the up/down controller flip-flops 152 and 154 to clock the counter in the up direction. Again the counter 52 will count up until a second pulse 402 is produced by the comparator 46. The direction of the counter is reversed again and the counter counts down until a CO pulse is produced as shown by arrow 406. This CO pulse will cause marker burst generator flip-flops 180 and 182 to produce a marker burst 408 by reason of the state of the validation flip-flop.

The reception of a succession of ultrasonic waves in response to a sequence of consecutive TRIG pulses will cause the validation flip-flop 158 to be clocked to its reset state following receipt of each TRIG pulse. Hence, a marker burst will be produced by multivibrator 180 in response to each of the successive ultrasonic waves. Once the biopsy probe fails to receive a detectable ultrasonic wave following a TRIG pulse, two consecutive receptions must occur before the validation flip-flop is again reset and a marker burst is produced.

The marker burst is applied to the line of cable 17 which conveys echo information pulses from the imaging probe 14 to the ultrasound system 16. Hence, the marker burst will be treated as a strong echo reception at the location of the stylet tip by the imaging system and will be displayed accordingly.

The BLINK signal produced by the timer 170 is applied to the clear input of the multivibrator 182 of the marker burst generator. The pulsing of the BLINK signal during reception of ultrasonic waves will periodically inhibit the multivibrator 182 from producing pulses. The resultant effect on the ultrasonic image display is that the visual marker will appear to blink off and on in synchronism with the pulsing of the BLINK pulse.

Figure 8:
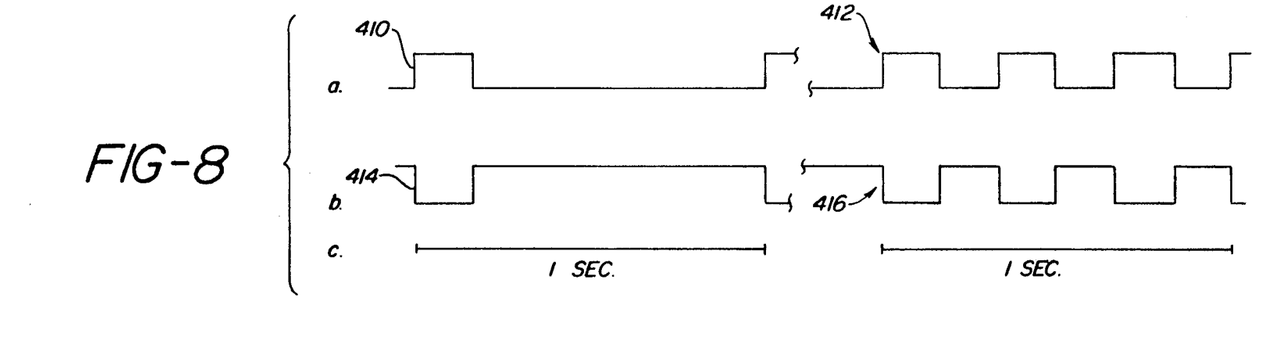

The BLINK signal is illustrated in FIG. 8b, and its inverse, which gates the audio oscillator 176 of the audible indicator, is shown in FIG. 8a. Both waveforms of these figures are drawn to the time scale of FIG. 8c. When only a small quantum of ultrasonic energy is being received, the visual marker will blink off for only one short interval each second, as indicated by low-going pulse 414. Correspondingly, the speaker 90 is gated by pulse 410 to produce only one short "beep" each second. But as the biopsy probe approaches the image plane in which the ultrasonic waves are directed, the intensity of the received ultrasonic energy increases, as does the rates of these pulses. The speaker 90 is then "beeped" at a higher rate, up to a maximum rate of three times per second by pulses 412, and the visual marker is blinked at the same higher rate by pulses 416. Thus, the physician is guided to the image plane by the increasing rates of these visual and audible indicators.

It may be appreciated that other audible indications other than periodic "beeps" may also be employed. For instance, by appropriate scaling of the output of comparator 166 of FIG. 5 and direct application of such a signal to the oscillator 176, the frequency of a continual pulse train produced by the oscillator may be varied. This would cause the oscillator to produce a low frequency as ultrasonic energy is first received, and a gradually increasing frequency as the image plane is approached, or the reverse. Alternatively, the intensity-variable signal produced by the comparator could be applied to a gain control input of amplifier 178, causing the production of a tone which changes from soft to loud in correspondence with the needle and image plane positions.

FIG. 6 also illustrates a test and calibration feature for transponder module and imaging system. This feature may be enabled prior to the initiation of a surgical procedure and prior to connecting the biopsy probe 20 to the transponder module 12 to verify operation of the module and calibrate the display on the imaging system 16. This feature is actuated by opening a switch 306, which enables monostable multivibrator 300 to be triggered by each TRIG pulse from the imaging system. Each TRIG pulse causes the Q-not output of multivibrator 300 to go low for a predetermined period of time which corresponds to the time required for an ultrasonic wave to travel a given distance from the imaging probe. For instance, the duration of the pulse of the multivibrator can be set to 18 microseconds to correspond to three centimeters of travel by an ultrasonic wave. The trailing edge of the pulse of the multivibrator 300 triggers the marker burst generator which transmits a marker burst by way of cable 17 to the imaging system at this time. In the present example, the timing of this burst would produce a visual marker at a depth of three centimeters below the skin line.

Production of a marker burst by the marker burst generator is enabled in the test and calibration mode by applying the TEST signal from inverter 308 to the clear input of validation flip-flop 158. The validation flip-flop is thereby held in a state to permit continual production of marker bursts during this mode of operation.

The marker burst produced by multivibrator 180 in the test and calibration mode is coupled by way of a diode 304 to be injected into the bandpass amplifier 142 of the preamplifier (see FIG. 4). This injected burst is received by the preamplifier and succeeding circuitry in the same manner as the reception of an ultrasonic wave by the biopsy probe 20. Hence, the injected burst serves to exercise the preamplifier, AGC amplifier, detector, comparator, and counter circuitry to verify their operation. When the module is operating properly the injected burst will be detected and will cause a reversal of the direction of the counter 52 at the marker burst time, which is approximately 19.5 microseconds in this example. The counter will then reverse the direction of its count and count down until a CO pulse is produced at the count of zero. The CO pulse, produced 19.5 microseconds after the reception of the injected burst, will trigger the production of a second marker burst at a timing for display at a depth of six centimeters below the skin line. Thus, during each TRIG pulse interval, two marker bursts will be sent to the imaging system, one at the end of the interval of the pulse of multivibrator 300 and another at twice that interval. In the present example the visual markers will be produced at image depths of three and six centimeters.

Figure 9:
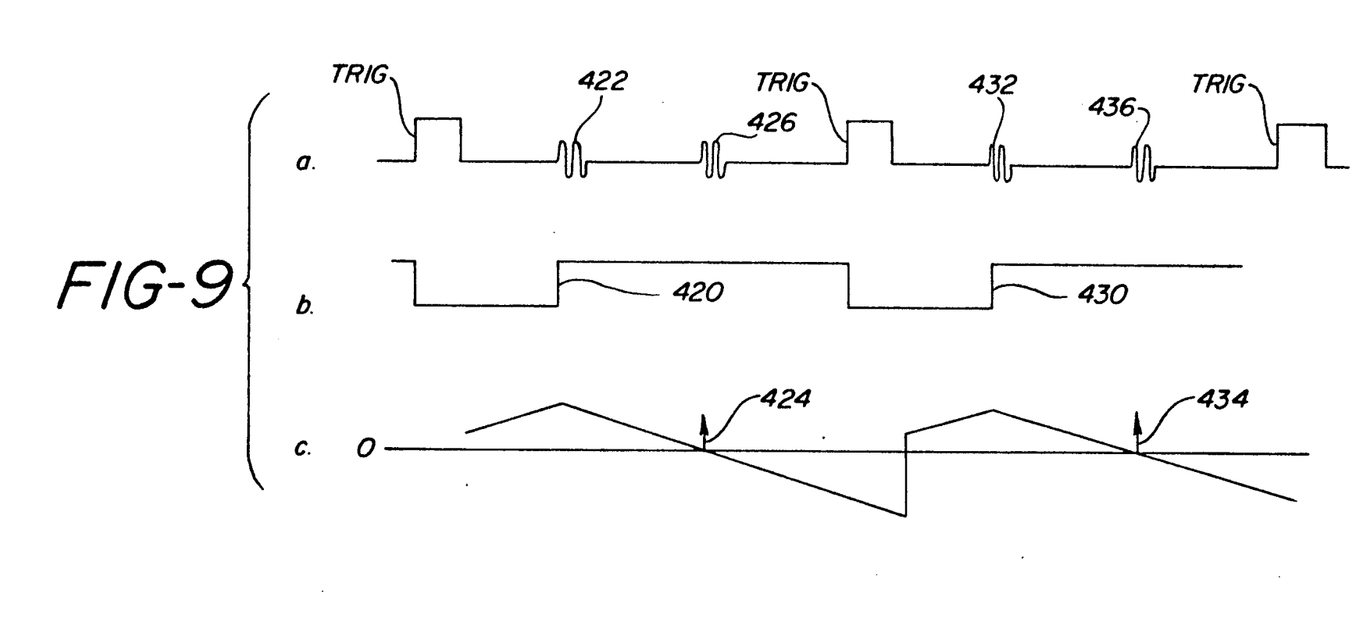

The sequence of operation of the test and calibration feature is illustrated by the waveforms of FIG. 9. FIG. 9a shows the signals on the cable 17, including the TRIG pulses received from the imaging system and the marker bursts transmitted to the imaging system by the module. FIG. 9b illustrates the pulses produced by the multivibrator 300, and FIG. 9c illustrates the count of the counter 52. At the end of the pulse 420, marker burst 422 is generated and transmitted to the imaging system. The marker burst 422 is also injected into the preamplifier, causing the counter 52 to begin counting down at this time. When the counter reaches zero as indicated by arrow 424, the CO pulse of the counter generates a second marker burst 426 which is transmitted to the imaging system. It may be noted that, while this second marker burst is also injected into the preamplifier, it does not propagate through to the detector. This is because the reception of the first injected marker burst 422 acted to set flip-flop 110, reducing the gain of the AGC amplifier to near zero. The AGC amplifier is not re-enabled until the next TRIG pulse is received and the flip-flop 110 is reset.

As the remainder of FIG. 9 illustrates, for each TRIG pulse two visual markers, e.g., 432 and 436, are produced on the image display at once and twice the multiples of the duration of pulses 420, 430.

The continual transmission of these visual markers to the imaging system will generate two lines across the image as shown in the exemplary test image of FIG. 1. Under proper operating conditions the two lines will appear at two depths in the displayed image, the greater depth being twice the lesser depth. In the present example the imaging system calipers should show the lines in the display at the indicated depths of three and six centimeters. If the image display does not show two lines at two depths, one being twice the other, the user is made aware of the need to calibrate or otherwise make adjustment to the transponder module before commencing with a surgical procedure.

What is claimed is:

1. An ultrasonic imaging system for depicting the location of a medical instrument within the body of a patient comprising:

an ultrasonic image display;
an ultrasonic imaging transducer coupled to said image display for transmitting ultrasonic waves into the body;
a medical instrument for use within the body and having an ultrasonic transducer associated therewith for reception of ultrasonic wave energy from said imaging transducer, said medical instrument ultrasonic transducer receiving maximal ultrasonic wave energy when located in the image plane of said ultrasonic imaging transducer;
means, responsive to reception of said ultrasonic wave energy by said medical instrument ultrasonic transducer, for producing an image display signal which is indicative of the location of said medical instrument ultrasonic transducer in the body;
means, coupled to said medical instrument ultrasonic transducer, for producing a signal which varies as a function of the ultrasonic wave energy received by said medical instrument ultrasonic transducer;

means for producing an audible tone; and means, responsive to said ultrasonic wave energy variable signal and coupled to said audible tone producing means, for modulating said tone as a function of the ultrasonic wave energy received by said medical instrument ultrasonic transducer.

2. The ultrasonic imaging system of claim 1, wherein said modulating means includes means for modulating said tone over a range of modulation bounded by maximal and minimal modulation levels, said maximal modulation level being employed when said medical instrument ultrasonic transducer is located in the image plane of said ultrasonic imaging transducer.

3. The ultrasonic imaging system of claim 2, wherein said modulating mean includes means for modulating said tone producing means to produce a pulsatile tone, said tone having a maximal pulsatile rate when modulated at said maximal modulation level.

4. The ultrasonic imaging system of claim 2, wherein said modulating means includes means for modulating said tone producing means to produce a pulsatile tone, said tone having a minimal pulsatile rate when modulated at said maximal modulation level.

5. The ultrasonic imaging system of claim 2, wherein said modulating means includes means for modulating said tone producing means to produce a variable frequency tone, said tone exhibiting a maximal frequency when modulated at said maximal modulation level.

6. The ultrasonic imaging, system of claim 2, wherein said modulating mean includes means for modulating said tone producing means to produce a variable frequency tone, said tone exhibiting a minimal frequency when modulated at said maximal modulation level.

7. The ultrasonic imaging system of claim 2, wherein said modulating means includes means for modulating said tone producing means to produce a variable volume tone, said tone exhibiting a minimal volume when modulated at said maximal modulation level.

8. The ultrasonic imaging system of claim 2, wherein said modulating means includes means for modulating said tone producing means to produce a variable volume tone, said tone exhibiting a maximal volume when modulated at said maximal modulation level.

9. An ultrasonic imaging system for depicting the location of a medical instrument within the body of a patient comprising:

an ultrasonic imaging transducer for transmitting and receiving ultrasonic waves over a planar interior region of the body;

a medical instrument for use within the body and having an ultrasonic transducer associated therewith for exchange of ultrasonic wave energy with said imaging transducer as said instrument transducer approaches and intersects said planar region;

amplitude detection means, responsive to the exchange of ultrasonic wave energy by said imaging and instrument transducers, for detecting the level of ultrasonic wave energy exchanged therebetween and producing a level signal representative thereof;

means, coupled to said amplitude detection means, for producing a variable signal which varies as a function of changes in the level of exchanged ultrasonic wave energy;

means for producing an audible tone; and means, responsive to said variable signal and coupled to said audible tone producing means, for modulating said tone as a function of changes in the level of ultrasonic wave energy exchanged by said imaging and instrument transducers.

10. The ultrasonic imaging system of claim 9, wherein said tone producing means includes means for producing a pulsatile tone, and the rate of said pulsatile tone is modulated by said modulating means.

11. The ultrasonic imaging system of claim 9, wherein said tone producing means includes means for producing a frequency variable tone, and the frequency of said tone is modulated by said modulating means.

12. The ultrasonic imaging system of claim 9, wherein said tone producing means includes means for producing a volume variable tone, and the volume of said tone is modulated by said modulating means.

13. An ultrasonic imaging system for depicting the location of a medical instrument within the body of a patient comprising:

an ultrasonic imaging transducer for transmitting ultrasonic waves over a planar interior region of the body;

a medical instrument for use within the body and having an ultrasonic transducer associated therewith for reception of ultrasonic wave energy from said imaging transducer as said instrument transducer approaches and intersects said planar region;

amplitude detection means, responsive to reception of ultrasonic wave energy by said instrument transducer, for detecting the level of received ultrasonic wave energy and producing a level signal representative thereof;

means, coupled to said amplitude detection means, for producing a variable signal which varies as a function of changes in the level of received ultrasonic wave energy;

means for producing an audible tone; and means, responsive to said variable signal and coupled to said audible tone producing means, for modulating said tone as a function of changes in the level of ultrasonic wave energy received by said instrument transducer.

14. In an ultrasonic imaging system for depicting the location of a medical instrument within the body of a patient, including imaging transducer means for producing imaging signals of an interior region of the body, an ultrasonic image display means for displaying a depth calibrated ultrasonic image of an interior region of the body in response to imaging signals produced by said imaging transducer means, an invasive medical instrument having an ultrasonic transducer affixed thereto for actuation within the body, and apparatus, coupled to said ultrasonic image display means and to said invasive medical instrument, for generating a visual marker in response to actuation of said ultrasonic transducer for display in said ultrasonic image indicating the location of said invasive medical instrument in said interior region, said apparatus further comprising:

actuation timing measurement means for measuring the time of actuation of said ultrasonic transducer of said invasive medical instrument; and means for generating a calibration signal, including means for coupling said calibration signal to said ultrasonic image display means for display calibration of said actuation timing measurement means in relation to said depth calibrated ultrasonic image.

15. The ultrasonic imaging system of claim 14, wherein said calibration signal is displayed at first and second depths on said image display means, said second depth being twice said first depth.

16. The ultrasonic imaging system of claim 14, wherein sad apparatus further comprises means for injecting a test signal which represents a received ultrasonic pulse into said apparatus for testing the operating condition of said apparatus.

17. The ultrasonic imaging system of claim 16, wherein said calibration signal is injected into said apparatus as said test signal.

18. The ultrasonic imaging system of claim 14, further comprising:

means, coupled to said imaging transducer means, for energizing said imaging transducer means to transmit a plurality of ultrasonic waves over said interior region of the body; and means for applying said calibration signal to said ultrasonic image display means following energizations of said imaging transducer means.

19. The ultrasonic imaging system of claim 18, wherein said calibration signal is applied to said ultrasonic image display means a predetermined time after actuation of said imaging transducer for display at a predetermined indicated depth on said image display means.

20. The ultrasonic imaging system of claim 19, wherein said calibration signal is applied to said ultrasonic image display means at first and second predetermined times after actuation of said imaging transducer for display at first and second indicated depths on said image display means.

* * * * *